(12) United States Patent
Patel et al.

(10) Patent No.: US 6,851,626 B2
(45) Date of Patent: Feb. 8, 2005

(54) METHODS AND DEVICES FOR NEBULIZING FLUIDS

(75) Inventors: Rajan Patel, Union City, CA (US); Michael Klimowicz, Escondido, CA (US); Paul Albulet, Santa Clara, CA (US); Nicanor A. Domingo, Brisbane, CA (US)

(73) Assignee: Aerogen, Inc., Mountain View, CA (US)

( * ) Notice: Subject to any disclaimer, the term of this patent is extended or adjusted under 35 U.S.C. 154(b) by 0 days.

(21) Appl. No.: 10/043,075

(22) Filed: Jan. 7, 2002

(65) Prior Publication Data

US 2003/0127538 A1 Jul. 10, 2003

(51) Int. Cl.⁷ .............................................. A61M 11/06
(52) U.S. Cl. .................. 239/338; 222/325; 128/200.24; 128/200.16; 128/898
(58) Field of Search .......................... 239/338; 222/325, 222/327, 402.2; 128/200.21, 200.22, 200.23, 200.16, 200.18, 200.12, 200.24, 200.26, 205.13, 898

(56) References Cited

U.S. PATENT DOCUMENTS

| | | | | |
|---|---|---|---|---|
| 3,838,686 A | * | 10/1974 | Szekely ...................... 239/338 |
| 5,115,803 A | * | 5/1992 | Sioutas .................. 128/200.23 |
| 5,435,282 A | * | 7/1995 | Haber et al. ................. 239/338 |
| 5,435,297 A | * | 7/1995 | Klein ..................... 128/200.23 |
| 5,755,218 A | * | 5/1998 | Johansson et al. ...... 128/200.14 |

* cited by examiner

Primary Examiner—Dinh Q. Nguyen
(74) Attorney, Agent, or Firm—Townsend and Townsend and Crew LLP (57) ABSTRACT

Devices and methods for nebulizing a fluid are described. A replaceable fluid assembly may include a reservoir and a fluid cartridge. The reservoir may be detachable from the fluid cartridge and may be assembled by the prior prior to loading into the nebulizing device.

12 Claims, 7 Drawing Sheets

METHODS AND DEVICES FOR NEBULIZING FLUIDS

BACKGROUND OF THE INVENTION

Field of the Invention

The present invention is directed to the field of devices for nebulizing fluids. In particular, the nebulizing device of the present invention is directed to an inhalation device for delivering a nebulized fluid.

The present invention is also directed to devices and methods for storing and delivering fluids to be nebulized.

SUMMARY OF THE INVENTION

The present invention provides a nebulizing device which is preferably a hand-held nebulizing device for inhalation of the nebulized fluid. The device has a mouthpiece through which the user inhales the nebulized fluid. The nebulizing element is preferably a vibrating element with holes through which the fluid is ejected although other suitable nebulizing elements may be used without departing from numerous aspects of the invention.

The fluid is held in a container which holds a number of doses of the fluid. The container delivers the fluid to a reservoir. The reservoir is designed to minimize the residual volume in the reservoir. The inner surface of the reservoir is preferably hydrophobic to encourage fluid to flow downward to the nebulizing element. The reservoir is also preferably tear-drop shaped and has a smooth inner surface which is free of seams and corners to further encourage downward flow. The container and reservoir may be replaced independently or at the same time. The reservoir and container may also be a single unit or may be separate units mounted to the device by the user.

The reservoir also has a collection area located adjacent to the vibrating element where a final volume of fluid accumulates. The final volume is drawn over the holes in the vibrating element when the vibrating element is vibrated thereby reducing the residual volume. The reservoir is also designed so that the nebulizing element is positioned at a relatively low hydrostatic position when the nebulizer is positioned in a preferred operating orientation. For example, the nebulizing element may be positioned so that less than 25%, and even less than 10%, of the volume of the reservoir is positioned below the nebulizing element.

The reservoir also has one or more vent holes for smooth fluid delivery into the reservoir during filling and out of the reservoir when the fluid is being nebulized. The vent hole is sized to prevent the fluid from escaping therethrough.

The fluid path between the container and reservoir includes a valve which prevents contamination of the container and fluid path. The valve maintains the sterility of the container so that the container does not need to be pierced a number of times as may otherwise be necessary. The valve may be positioned at a wall of the reservoir so that the valve isolates the entire fluid path together with the container.

Various aspects of the present invention are also directed to a container. The container is similar to a standard vial with the addition of a specialized connector. The connector mates with the nebulizing device and, in another aspect, may mate with the reservoir as well. The connector has a protrusion which engages an L-shaped slot in the device for a bayonette-type connection. The connector also has a number of tabs or hooks which engage the reservoir to lock the reservoir to the container.

The mouthpiece may be separable from the rest of the housing. The nebulizing element may also be contained within the mouthpiece so that the nebulizing element may be cleaned along with the mouthpiece. The mouthpiece also has a port which receives a pressure sensing conduit. The pressure sensing conduit leads from a mouthpiece chamber to a pressure sensor. The pressure sensor is used for breath-actuation of the device by sensing the drop in pressure when the user inhales on the mouthpiece.

These and other aspects of the invention are disclosed and described in the following description, drawings and claims.

DETAILED DESCRIPTION OF PREFERRED EMBODIMENTS

Referring to FIGS. 1–8, a nebulizing device 2 is shown. The nebulizing device 2 is preferably a hand-held inhalation device although various aspects of the invention may be practiced with any other nebulizing device or inhalation device. The nebulizing device 2 has a housing 4 which includes a mouthpiece 6 through which the user inhales a nebulized fluid. The fluid is nebulized by a nebulizing element 8 and the nebulized fluid is entrained in air drawn into the device 2 through air inlet openings 10 in the mouthpiece 6.

The fluid to be nublized is a container 12, such as vial 15, which preferably holds a number of doses of the fluid. The container 12 and replaced as necessary. The user selects a dose size or amount and delivers the dose from the container 12 to a reservoir 14, which holds fluid. The reservoir 14 may be removed and replaced together with or separate from the container 12 as explained below.

The container 12 has a piston 16, which is moved by dosing mechanism 18 to dispense a volume of the fluid. The dosing mechanism 18 may be any suitable dosing mechanism such as the dosing mechanism for insulin pen mechanisms. The dosing mechanism 18 is operated with a dosing control 20 which the user operates to select and deliver a quantity of fluid to the reservoir 14. the housing 4 has a window to view the amount of fluid in the container 12.

Figure 5:
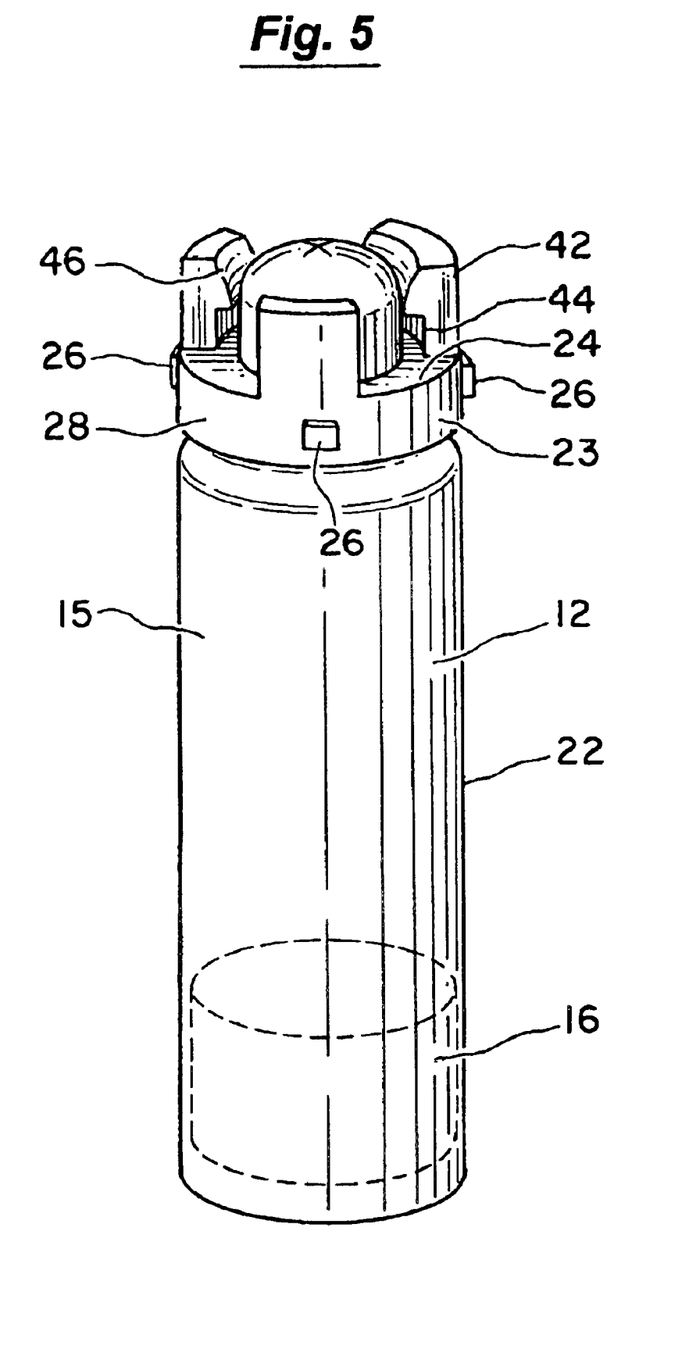
FIG. 5 shows the container.

The container 12 has a body 22 similar to a standard vial. The container 12 does differ from a standard vial in that the container 12 has a connector 23, such as a collar 24, which mates with the reservoir 14 and the nebulizer 2. The connector 23 helps to prevent the user from loading the wrong fluid into the nebulizer 2. To this end, the connector 23 has a bayonet-type connection with the nebulizer 2. The connector 23 has three projections 26 extending from a cylindrical body 28. The projections register and slide within L-shaped 30 slots in the nebulizer 2. The container 12 is loaded into the device 2 by pushing downward and then rotating the collar 24 to secure the collar 24, and therefore container 12, to the device 2. The slots 30 may have a raised-portion or detent to lock the projection in the slot 30. The position, size, spacing and orientation of the projections 26 and corresponding slots 30 may be altered for different fluids to prevent use of the improper fluid. The device 2 may also have a sensor 32 which detects proper engagement of the projection 26 within the slot 30 before the device 2 will dispense fluid. The container 12 may, of course, have any suitable connection with the nebulizer 2 which helps to prevent use of the improper fluid.

The container 12 also locks together with the reservoir 14 to provide a secure engagement with the reservoir. When the container 12 is mounted to the reservoir 14, a needle 40 pierces the container 12. The container also has three tabs or hooks 42 which lock together with mating connectors on the reservoir 14. The tabs 42 are located about 120 degrees apart and each have a recess 44 and a shoulder 46 which engage complemtary features on a connector 43 on the reservoir 14. The container 12 and reservoir 14 may, of course, mount to one another in any other suitable manner and the features may be altered for different fluids.

Figure 1:
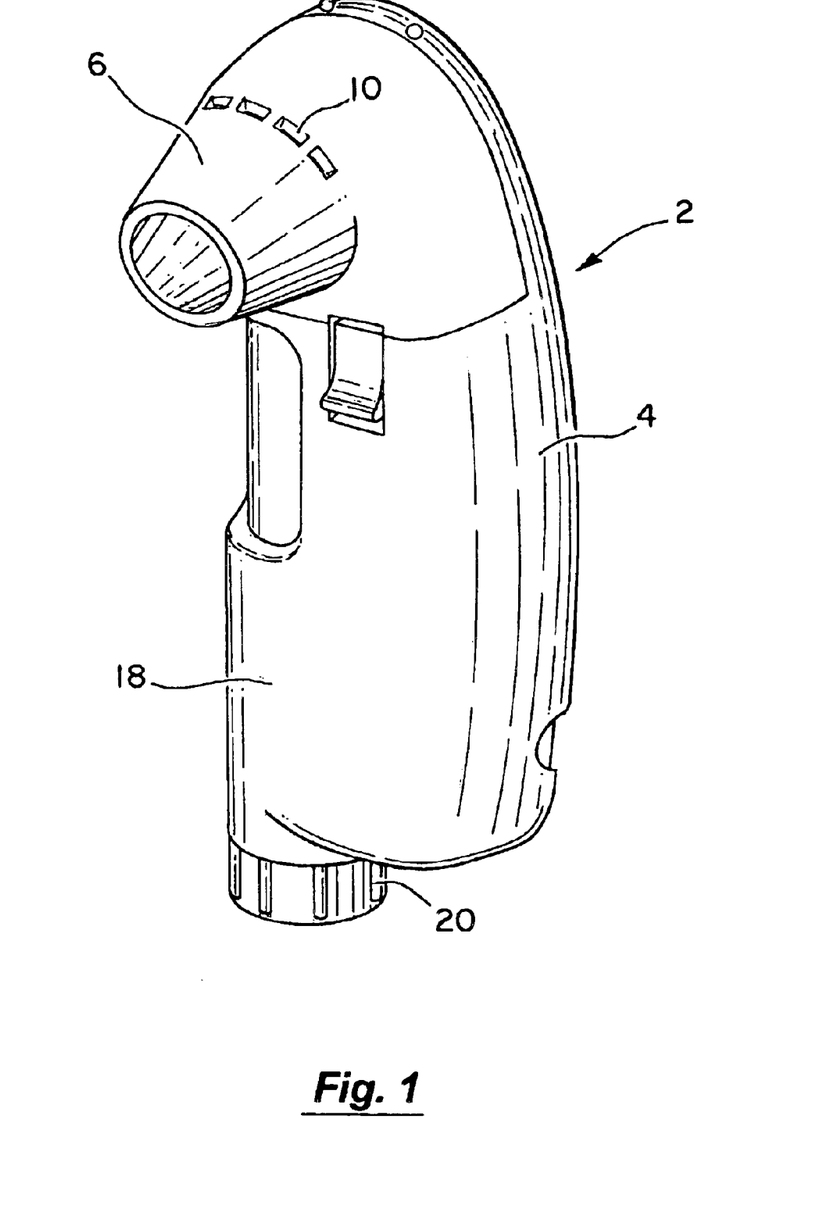
FIG. 1 shows a nebulizer.
Figure 2:
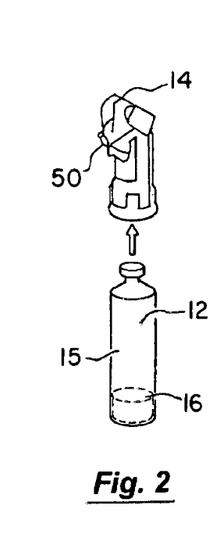
FIG. 2 shows a fluid assembly formed by a reservoir and a container.
Figure 3:
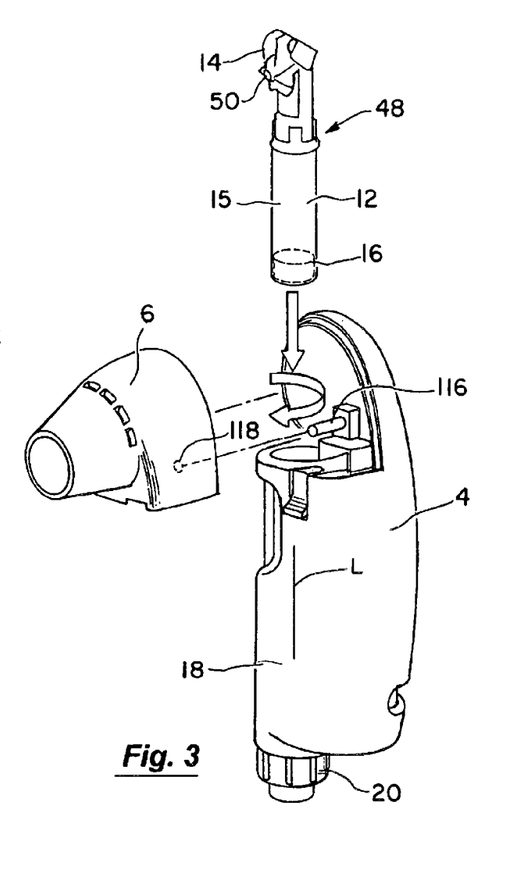
FIG. 3 shows the nebulizer with a mouthpiece and fluid assembly removed.
Figure 4:
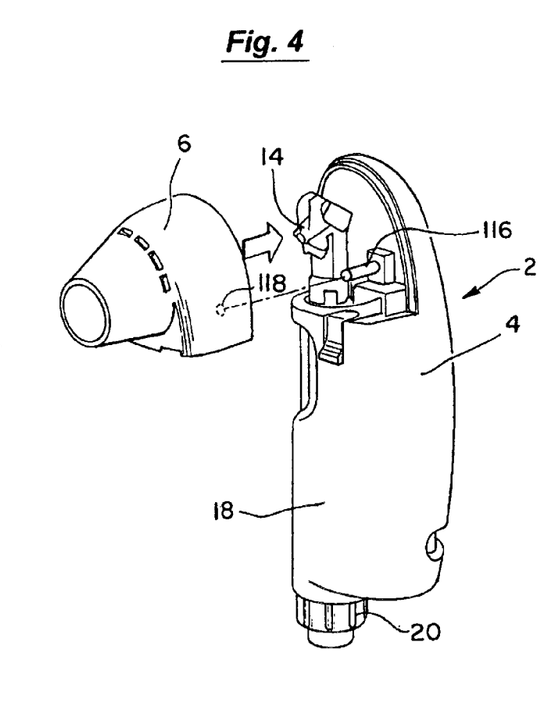
FIG. 4 show the fluid assembly mounted to the nebulizer with the mouthpiece removed.

The container 12 and reservoir 14 form a fluid assembly 48. The container 12 is preferably mounted to the reservoir 14 by the user immediately before loading the container 12 and reservoir 14. Alternatively, the container 12 and reservoir 14 may be loaded sequentially. For example, the container 12 could be mounted to the device 2 followed by mounting the reservoir 14 to the container 12. The fluid assembly 48 may also be provided as a single unit which the user replaces all at once.

Figure 6:
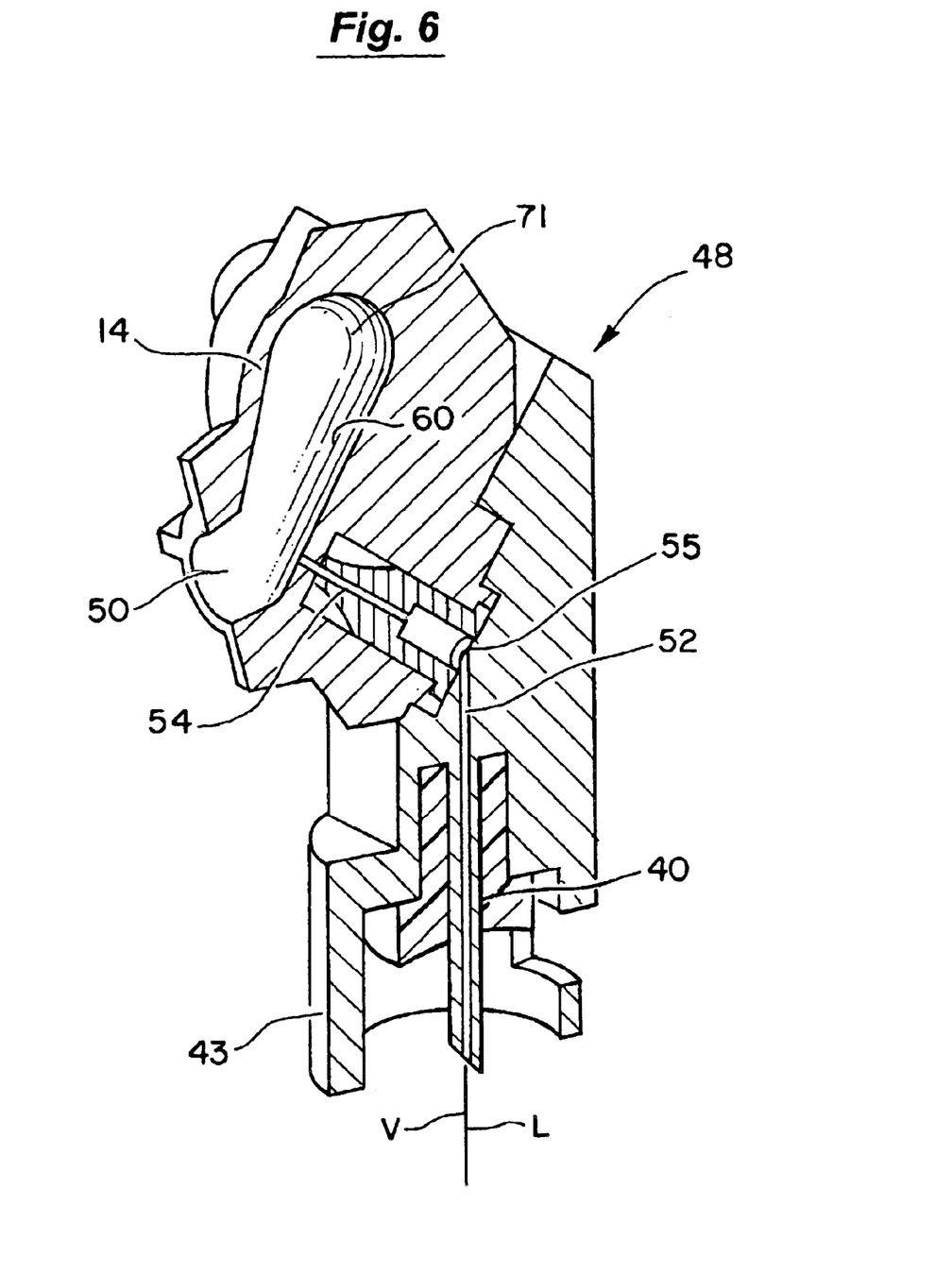
FIG. 6 is a perspective, cross-sectional view of the reservoir.

The reservoir 14 has an opening 50 which delivers the fluid to the nebulizing element 8. The opening 50 is oriented to form a feed angle of about 5 to 30 degrees, and may be about 15 degrees, relative to the longitudinal axis L of the container 12 as defined by the container 12 body. The opening 50 also may have a diameter of about 0.05 to 0.25 inch and may be about 0.15 inch. The opening 50 size and feed angle provide smooth delivery of the fluid from the reservoir 14 to the nebulizing element 8 particularly when the nebulizing element 8 is oriented somewhat upright.

The fluid travels along a fluid path 52 between the container 12 and reservoir 14. The fluid path 52 includes the needle 40 and a channel leading from the needle 40 to the reservoir 14. The fluid path 52 may, of course, be formed in any other manner including a simple lumen or tube extending between the container 12 and reservoir 14. Furthermore, the fluid coupling between the container 12 and reservoir 14 may be any other suitable coupling other than needle 40.

The fluid path 52 also includes a valve 54 which prevents contamination of the container 12. The valve 54 eliminates the need to pierce the container 12 a number of times as may be necessary to maintain sterility if the valve were not provided. The valve 54 may be a one-way valve such as a slit valve, ball valve or duckbill valve. The valve 54 is preferably positioned to protect the entire fluid path between the container 12 and reservoir 14. To this end, the valve 54 may be positioned at the end of the fluid path 52 such as at a wall 56 of the reservoir 14. The valve 54 may also be positioned at a relatively low hydrostatic position relative to the reservoir 14 such that less than 25% of the reservoir 14, and more preferably less than 10%, is positioned hydrostatically below the valve 54. In this manner, the residual fluid volume in the reservoir 14 may be reduced since the valve 54 position can reduce the wetted surface of the reservoir 14 as compared to a valve positioned to dispense the fluid at a higher position in the reservoir. Of course, the valve 54 may be positioned at an elevated position in the reservoir 14 without departing from the invention. The valve 54 may also direct the fluid at the nebulizing element 8. The valve 54 may direct a stream of fluid at the nebulizing element 8 so that air in the reservoir 14 near the nebulizing element 8 is actively removed. A problem which can occur when delivering fluid to the nebulizing element is that air can be trapped near the nebulizing element which can inhibit proper functioning of the device. The orientation of the valve 54 and the ability of the valve 54 to deliver a stream of fluid together reduce the risk of trapping air around the nebulizing element 8.

The reservoir 14 has an inner wall 71 that has a tear-drop shape and is substantially free of corners, seams and edges to encourage fluid drainage. The reservoir 14 has a backwall 60 which forms an angle of about 20 to 70 degrees with respect to horizontal when the device is held in a preferred operating orientation. The inner wall 62 of the reservoir 14 is also preferably hydrophobic, but may be hydrophilic depending upon the application and particular fluid, to further reduce the residual volume. The reservoir 14 may also have a relatively small volume to minimize the surface area of the reservoir 14. The tear-drop shape, smooth interior wall, angled backwall 60 and hydrophobic surface all encourage liquid in the reservoir 14 to flow downward toward the nebulizing element 8 thereby minimizing the residual fluid volume.

The nebulizing element 8 may be angled away from the reservoir 14 at an angle of about 0–45 degrees relative to vertical and may be about 15 degrees when the device is in the preferred operating orientation. The reservoir 14 may be made in any suitable manner and with any suitable materials. For example, the reservoir 14 may be made out of polypropylene and formed by injection molding. The nebulizing element 8 may be oriented in any other manner and may be any type of nebulizing element.

Figure 7:
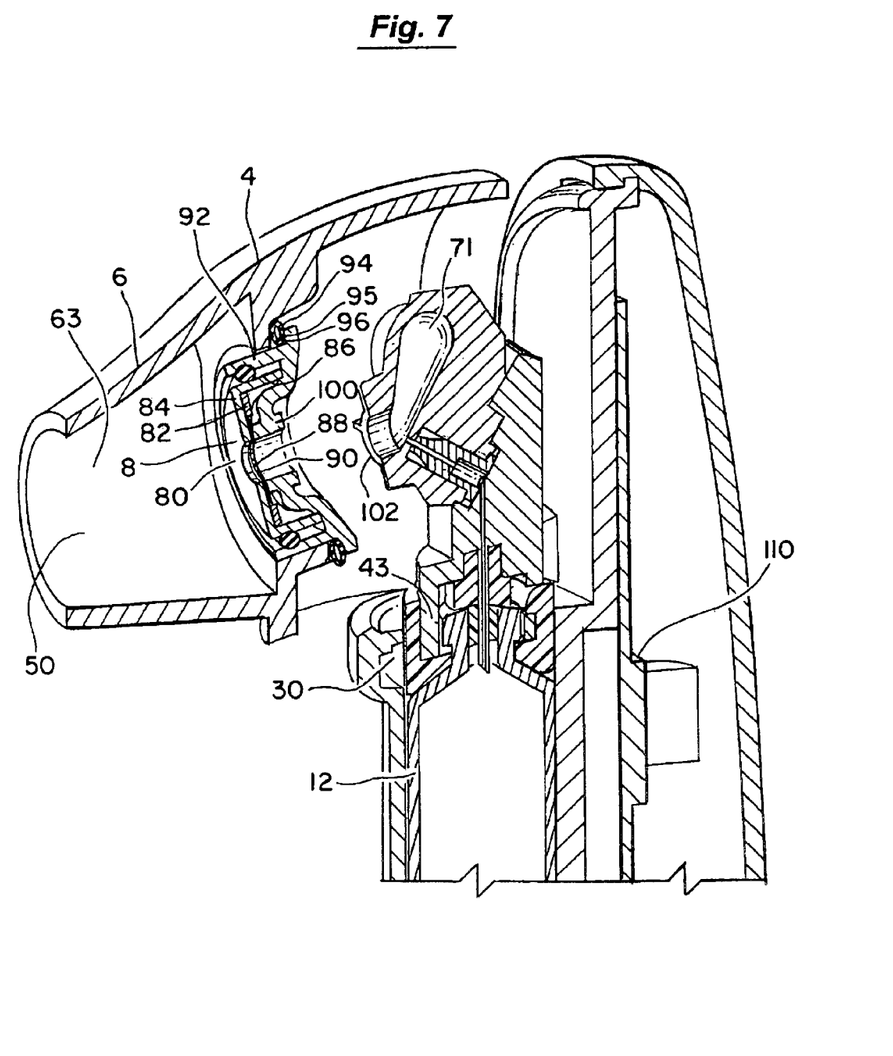
FIG. 7 is the perspective view of device with the mouthpiece removed.
Figure 8:
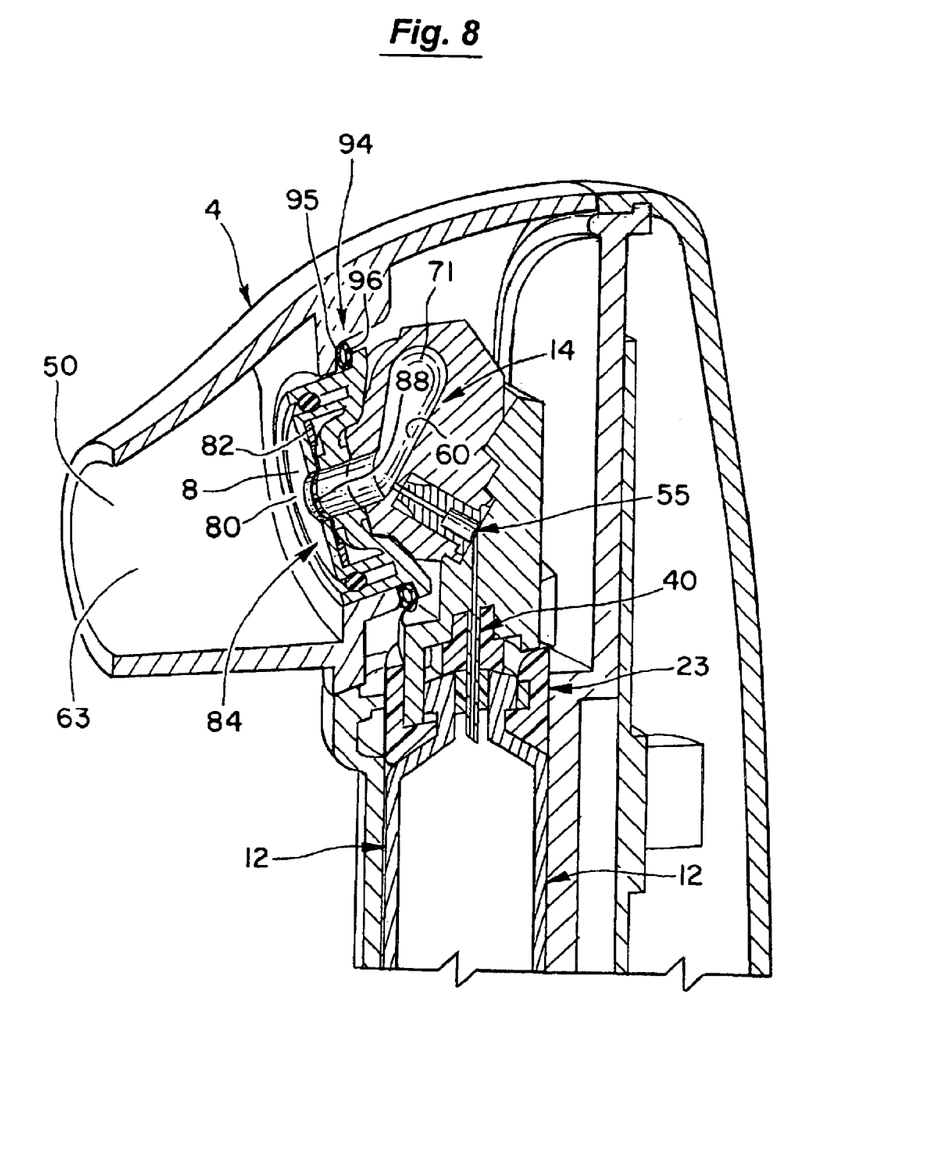
FIG. 8 is a perspective view of FIG. 7 with the mouthpiece attached to the housing.

The mouthpiece 6 may be removable to load and remove the container 12 and/or reservoir 14. Removal of the mouthpiece 6 also permits cleaning of the mouthpiece 6 and nebulizing element 8. The nebulizing element 8 may be cleaned or removed after each use or at any predetermined interval such as, for example, after a predetermined number of containers 12 and/or reservoirs 14 have been used. The mouthpiece 6 or nebulizing element 8 may even be removed and replaced with each container 12 or assembly 48. The mouthpiece 6 may be mounted with a suitable connection such as a snap-fit connection or latch with the rest of the housing.

The mouthpiece 6 has the air inlet opening 10, preferably a number of openings 10, which permit introduction of air to entrain the nebulized fluid for inhalation by the user. The nebulized fluid is entrained in the air entering a mouthpiece chamber 63 and the nebulized fluid is inhaled by the user when the user inhales on the mouthpiece.

The nebulizing element 8 may include a vibrating assembly 80. The vibrating assembly 80 includes a piezoelectric element 82 mounted to a substrate 84. The substrate 84 may be cup-shaped 86 or may have any other suitable shape such as a flat-ring or plate. A vibrating element 88 with a number of holes 90 is mounted to the substrate 84. The vibrating element 88 is preferably dome-shaped and the holes 90 may be tapered. The vibrating element 88 and assembly 80 may, of course, be any other suitable element such as a flat-plate, thin mesh or flexible membrane without departing from the scope of the invention. Furthermore, various aspects of the invention may be practiced independent of the particular nebulizing method and device.

The substrate 84 is coupled to the mouthpiece directly or by a mounting element 92 which secures the vibrating assembly 80 to the housing 4 and specifically the mouthpiece 6. The vibrating assembly 80, via the mounting element 92, is coupled to the housing 4 by a flexible connection 94 such as a resilient connection 95. The connection 94 may be formed in part by a spring, foam, or elastomeric element disposed between the vibrating assembly 80 and housing 4. In the particular embodiment shown, an elastomeric element 96 having an oval cross-section is shown although a C-shaped cross-section or other suitable shape may be used such as U-shaped. The flexible or resilient connection 94 can reduce dampening of the vibrating assembly as compared to rigid connections with the mouthpiece or housing 6.

The resilient connection 95 also provides a modest closing force on a fluid seal 98 between the nebulizing element 8 and reservoir 14. The closing force created by the resilient connection 95 helps to prevent fluid from leaking out of the seal 98 between the reservoir 14 and nebulizing element 8. The seal 98 is formed by a sealing element 100, such as an o-ring on the mounting element 92, and a complementary sealing element 102, such as a groove on the reservoir 14. The connection 94 naturally biases the sealing elements 100, 102 together in that the connection 94 is slightly compressed when the reservoir 14 is mounted. The proper alignment of the reservoir 14 is achieved when the mouthpiece 6 registers with the rest of the housing 4.

The mounting element 92 may also engage the vibrating assembly 80, such as the vibrating element 88, and direct fluid to the vibrating element 88. The mounting element 92 may engage the vibrating element 88 with any suitable connection. For example, the mounting element may be glued to the vibrating element 88 or may have an o-ring which engages the vibrating element. As mentioned above, the vibrating element is generally oriented within 45 degrees of vertical, and preferably about 15 degrees, during operation but may be oriented at any other angle without departing from the invention.

The device 2 is preferably breath-actuated in any suitable manner. In the preferred embodiment, a pressure sensor 110, such as a pressure transducer 112, measures pressure in the mouthpiece chamber 114 so that when the user inhales on the mouthpiece 6 the sensor 110 detects the pressure drop and triggers the nebulizing element 8 at a trigger pressure. The pressure sensor 110 may be mounted to the mouthpiece 6 but is preferably mounted to the body of the device 2. A pressure sensing conduit 116 extends to a rear chamber 118 of the device 2 where the pressure sensor 110 is mounted. A pressure sensing port 118 in the mouthpiece 6 receives the conduit 116 to provide pressure communication between the mouthpiece chamber 63 and pressure sensor 110 via the conduit 116.

Operation of the device is now described. The user detaches the mouthpiece and loads the fluid assembly into the device. The fluid assembly may be formed by the container and reservoir which are attached together by the user or mounted in sequence to the device. Once the container and reservoir are attached together, the interlocking feature may prevent disassembly and thus prevent improper usage of the device and parts thereof. The device may be primed in any suitable manner. For example, a volume of fluid equal to or just larger than the fluid path may be delivered when the container is loaded or when the first dose is delivered from a particular container. Alternatively, fluid may simply be delivered from the container until fluid is sensed in the reservoir.

Figure 9:
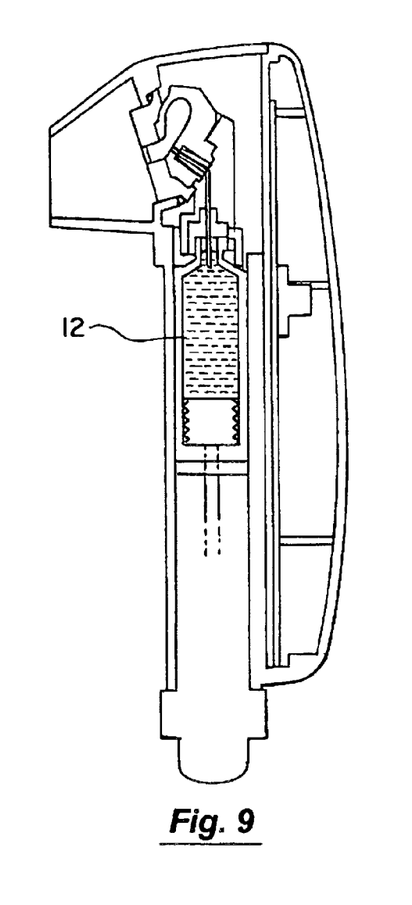
FIG. 9 is a cross-sectional view of the nebulizer with the reservoir empty.
Figure 10:
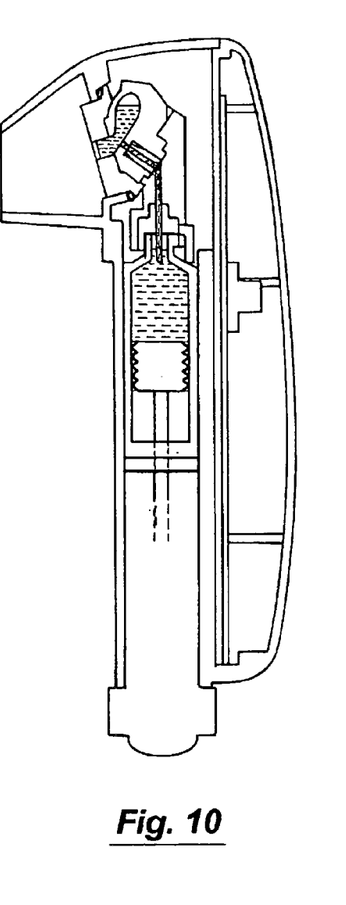
FIG. 10 is a cross-sectional view of the nebulizer with the reservoir filled with a volume of fluid.
Figure 11:
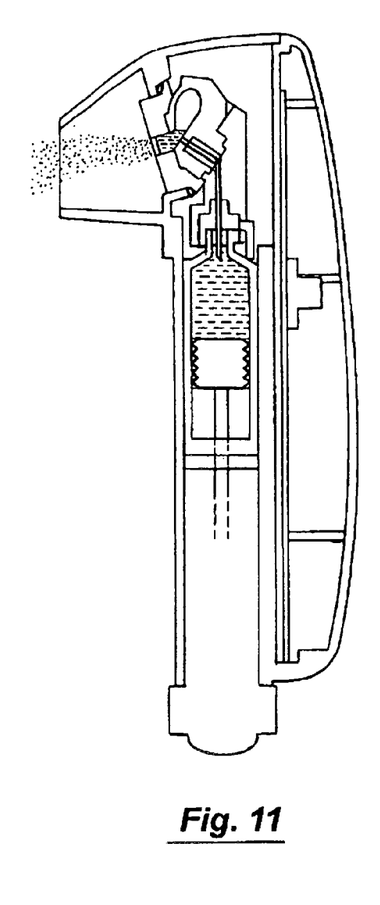
FIG. 11 shows the nebulizing element delivering the nebulized fluid through the mouthpiece.

When the user is prepared to inhale the nebulized fluid, the user operates the dosing controls to select and deliver a volume of fluid from the container to the reservoir. The dosing mechanism moves the piston to move fluid through the fluid path, out the valve and into the reservoir as shown in FIGS. 9 and 10. The user then operates the device by simply inhaling on the mouthpiece. When the user inhales, the pressure sensor detects the drop in pressure until the trigger pressure is reached at which time the nebulizing element is activated. Air is drawn into the chamber through the inlet openings and the nebulized fluid is entrained in the air which is inhaled by the user. The device continues to nebulize fluid while the user continues to inhale. This process is repeated until all of the solution has been nebulized. The device may also measure, detect or calculate when all of the fluid in the reservoir has been nebulized in any suitable manner. For example, the device may deactivate the nebulizing element by measuring the resonant frequency of the vibrating element before fluid is delivered and deactivating the nebulizing element just before the dry resonant frequency is reached again.

The invention has been described with respect to various specific embodiments but it can be appreciated that various modifications may be made without departing from the scope of the invention.

What is claimed is:

1. A method of delivering a nebulized fluid for inhalation, comprising the steps of:
   providing a nebulizing device, a reservoir and a container, the reservoir and container being adapted for holding volumes of fluids and being replaceable;
   delivering a volume of fluid corresponding to a selected dose size from the container to the reservoir;
   transferring the volume of fluid from the reservoir to the nebulizing device;
   using the nebulizing device to nebulize the volume of fluid;
   repeating the delivering and using steps a number of times with the same container;
   removing and replacing the container; and
   removing and replacing the reservoir.

2. The method of claim 1, wherein:
   the providing step is carried out with the nebulizing device having a vibrating element with a plurality of holes, the reservoir holding a fluid in contact with the vibrating element.

3. The method of claim 1, wherein:
   the removing and replacing steps are carried out with the reservoir being mounted to the container by the user which is followed by the user mounting both components together into the nebulizing device.

4. The method of claim 1, wherein:
   the providing step is carried out with reservoir having a needle which penetrates the container thereby providing a fluid path between the container and the reservoir.

5. The method of claim 1, wherein:

the providing step is carried out with a one-way valve positioned along a fluid path between the container and the reservoir.

6. The method of claim 5, wherein:

the providing step is carried out with the nebulizing device having a vibrating assembly, the vibrating assembly having a plurality of holes therein; and the delivering step is carried out with the valve directing the fluid at the vibrating assembly; and the using step is carried out with the fluid passing through the holes in the vibrating assembly.

7. The method of claim 5, wherein:

the delivering step is carried out with the valve delivering a stream of the fluid.

8. The method of claim 7, wherein:

the delivering step is carried out with the stream of fluid being directed at a vibrating assembly of the nebulizing device.

9. The method of claim 5, wherein:

the providing step is carried out with the valve positioned at the end of the fluid path so that the valve leads directly into the reservoir.

10. The method of claim 1, further comprising the step of:

removing a mouthpiece before the removing steps to permit at least one of the reservoir and the container to be removed and replaced.

11. The method of claim 10, wherein:

the removing steps are carried out with the reservoir and the container being separate units.

12. The method of claim 11, wherein:

the removing steps are carried out with the reservoir being mounted to the container by the user.

* * * * *